US009517286B1

(12) United States Patent
Li

(10) Patent No.: US 9,517,286 B1
(45) Date of Patent: Dec. 13, 2016

(54) AROMA DIFFUSING SYSTEM AND AROMA DIFFUSING METHOD THEREOF

(71) Applicant: Puzhen Life Co., Limited, Hong Kong (HK)

(72) Inventor: Dong Sheng Li, Hong Kong (HK)

(73) Assignee: PUZHEN LIFE CO., LIMITED, Hong Kong (HK)

( * ) Notice: Subject to any disclaimer, the term of this patent is extended or adjusted under 35 U.S.C. 154(b) by 0 days.

(21) Appl. No.: 15/093,723

(22) Filed: Apr. 7, 2016

(30) Foreign Application Priority Data

Mar. 21, 2016 (CN) .......................... 2016 1 0160666

(51) Int. Cl.
| | |
|---|---|
| *A62C 5/02* | (2006.01) |
| *A61L 9/14* | (2006.01) |
| *G08C 17/02* | (2006.01) |
| *H04W 76/02* | (2009.01) |
| *B05B 7/24* | (2006.01) |

(52) U.S. Cl.
CPC .............. *A61L 9/145* (2013.01); *B05B 7/2416* (2013.01); *B05B 7/2429* (2013.01); *G08C 17/02* (2013.01); *H04W 76/02* (2013.01); *A61L 2209/134* (2013.01)

(58) Field of Classification Search
CPC .. A61L 9/145; A61L 2209/134; B05B 7/2416; B05B 7/2429; G08C 17/02; H04W 76/02
USPC ............. 239/8, 11, 340, 351, 355, 360, 361, 366,239/368, 369, 302, 305; 352/85
See application file for complete search history.

(56) References Cited

U.S. PATENT DOCUMENTS

| | | | | |
|---|---|---|---|---|
| 6,672,129 | B1* | 1/2004 | Frederickson | A61M 15/02 73/23.34 |
| 7,878,418 | B2* | 2/2011 | Sevy | A61M 11/06 239/340 |
| 7,913,933 | B2* | 3/2011 | Van Roemburg | B05B 7/0012 239/338 |
| 2010/0309434 | A1* | 12/2010 | Van Schijndel | A61L 9/125 352/85 |

FOREIGN PATENT DOCUMENTS

CN 104977910 A 10/2015

OTHER PUBLICATIONS

Search Report issued by the Chinese Patent Office on Apr. 22, 2016.

* cited by examiner

*Primary Examiner* — Steven J Ganey

(57) ABSTRACT

The present invention relates to an aroma diffusing system and aroma diffusing method thereof. This method includes establishing wireless communication connection between a mobile terminal and an aroma diffuser; receiving user input and generating a corresponding order through the mobile terminal and sending the order in a wireless mode; receiving the order through the wireless communication module of the aroma diffuser and executing the order through the electric control element of the aroma diffuser; feeding back order execution result to the mobile terminal through the wireless communication module of the aroma diffuser; receiving the order execution result through the mobile terminal and giving a corresponding prompt in the mobile terminal. The present invention may control the operation mode of the aroma diffuser and improve operation experience and use experience through a smart phone.

9 Claims, 9 Drawing Sheets

AROMA DIFFUSING SYSTEM AND AROMA DIFFUSING METHOD THEREOF

CROSS-REFERENCE TO RELATED APPLICATIONS

The present application claims the benefit of Chinese Patent Application No. 201610160666.2 filed on Mar. 21, 2016, the contents of which are hereby incorporated by reference.

TECHNICAL FIELD

The present invention relates to an aroma diffusing system and aroma diffusing method thereof.

DESCRIPTION OF THE BACKGROUND

Aroma diffusers make use of the unique charm of fragrance and extend communication from vision and hearing to smell and even deeper layers. Consumers wish aroma diffusers more intelligent and more user-friendly.

SUMMARY OF THE INVENTION

On the one hand, the present invention provides a user-friendly aroma diffusing method, comprising the following steps: establishing wireless communication connection between a mobile terminal and an aroma diffuser; receiving user input and generating a corresponding order through the mobile terminal and sending the order in a wireless mode; receiving the order through the wireless communication module of the aroma diffuser and executing the order through the electric control element of the aroma diffuser.

As a modification to the present invention, the aroma diffusing method further comprises: feeding back order execution result to the mobile terminal through the wireless communication module of the aroma diffuser; receiving the order execution result through the mobile terminal and giving a corresponding prompt in the mobile terminal.

As a modification to the present invention, the aroma diffuser comprises at least two essential oil bottles for accommodating essential oil; the aroma diffuser further comprises gasification elements corresponding to the essential oil bottles and each of the gasification elements is used to extract essential oil from the corresponding essential oil bottle and gasify it. The orders include the orders for controlling gasification efficiency of corresponding gasification elements.

As a modification to the present invention, The orders include any of the following orders or combinations of two or more orders: order for shutting down or starting part or all of the gasification elements; order for controlling the time of continuous operation of part or all of the gasification elements; order for controlling cyclic operation of part or all of the gasification elements; order for controlling lighting color of the aroma diffuser; order for starting or shutting down part or all of the gasification elements at a fixed time.

As a modification to the present invention, the aroma diffusing method further comprises identifying picture color in the mobile terminal; the step of generating a corresponding order includes generating a corresponding lighting color order according to the color; the step of executing the order through the electric control element of the aroma diffuser includes regulating lighting of the aroma diffuser according to the lighting color order.

As a modification to the present invention, the aroma diffusing method further comprises playing video in the mobile terminal; the step of generating a corresponding order includes generating a corresponding lighting color order according to the video picture; the step of executing the order through the electric control element of the aroma diffuser includes regulating lighting of the aroma diffuser according to the lighting color order.

As a modification to the present invention, the aroma diffusing method further comprises the following steps: reading an audio file in the mobile terminal and sending out an audio signal in a wireless mode; receiving the audio signal through the wireless communication module of the aroma diffuser and playing the audio signal through the loudspeaker of the aroma diffuser.

On the second hand, the present invention provides a user-friendly aroma diffusing system. The system comprises an aroma diffuser. The aroma diffuser comprises essential oil bottles for accommodating essential oil, gasification elements for extracting essential oil from the essential oil bottles and gasifying the extracted essential oil and an electric control element for controlling the gasification elements, characterized in that the electric control element comprises a wireless communication module, used to receive orders sent in a wireless mode and executed by the electric control element.

As a modification to the present invention, there are at least two essential oil bottles and they are used to accommodate different essential oils; the quantity of the gasification elements is same as the quantity of the essential oil bottles and each of the gasification elements corresponds to an essential oil bottle; the electric control element may independently control the start, shutdown and gasification speed of each of the gasification elements.

As a modification to the present invention, the electric control element at least comprises one of the following switches: power switch used to connect or disconnect the gasification elements according to the order the wireless communication module receives; timing switch used to control the gasification elements according to the order the wireless communication module receives; lighting switch used to control the lighting of the aroma diffuser at a fixed time according to the order the wireless communication module receives; music switch used to control the loudspeaker of the aroma diffuser at a fixed time according to the order the wireless communication module receives.

As a modification to the present invention, the aroma diffuser further comprises a mobile terminal for wireless communication with the aroma diffuser and the mobile terminal is used to send orders for execution of the electric control element to the aroma diffuser in a wireless mode.

In preferred embodiments of the present invention, users may operate the aroma diffuser through a smart phone, including different essential oil proportions and lighting and music corresponding to scenes, to improve operation experience and use experience.

Where: 1, housing; 2, essential oil bottle; 3, centralized fragrance diffusion outlet; 4, gasification chamber body; 5, gasification chamber; 6, air chamber; 7, essential oil nozzle; 8, oil conduit; 9, air nozzle; 10, gasification chamber cover; 11, cavity; 12, fragrance outlet; 13, mixing chamber cover; 14, mixing blade; 15, mixing chamber base; 16, fragrance converging port; 17, fragrance access passage; 18, fragrance inlet; 19, pump mounting rack; 20, pump body; 21, air duct; 22, holder; 23, air output nozzle; 24, mounting hole; 25, support plate; 26, first groove; 27, second groove; 28, lower vortex body; 29, upper vortex body; 30, pressure plunger; 31, annular flange; 32, O ring; 33, pump cover; 34, cover groove; 35, control panel; 36, pump flow regulating button; 37, time setting button; 38, power switch; 39, air inlet.

DETAILED DESCRIPTION OF PREFERRED EMBODIMENTS

Below the present invention will be further described by referring to the accompanying drawings and embodiments.

Figure 1:
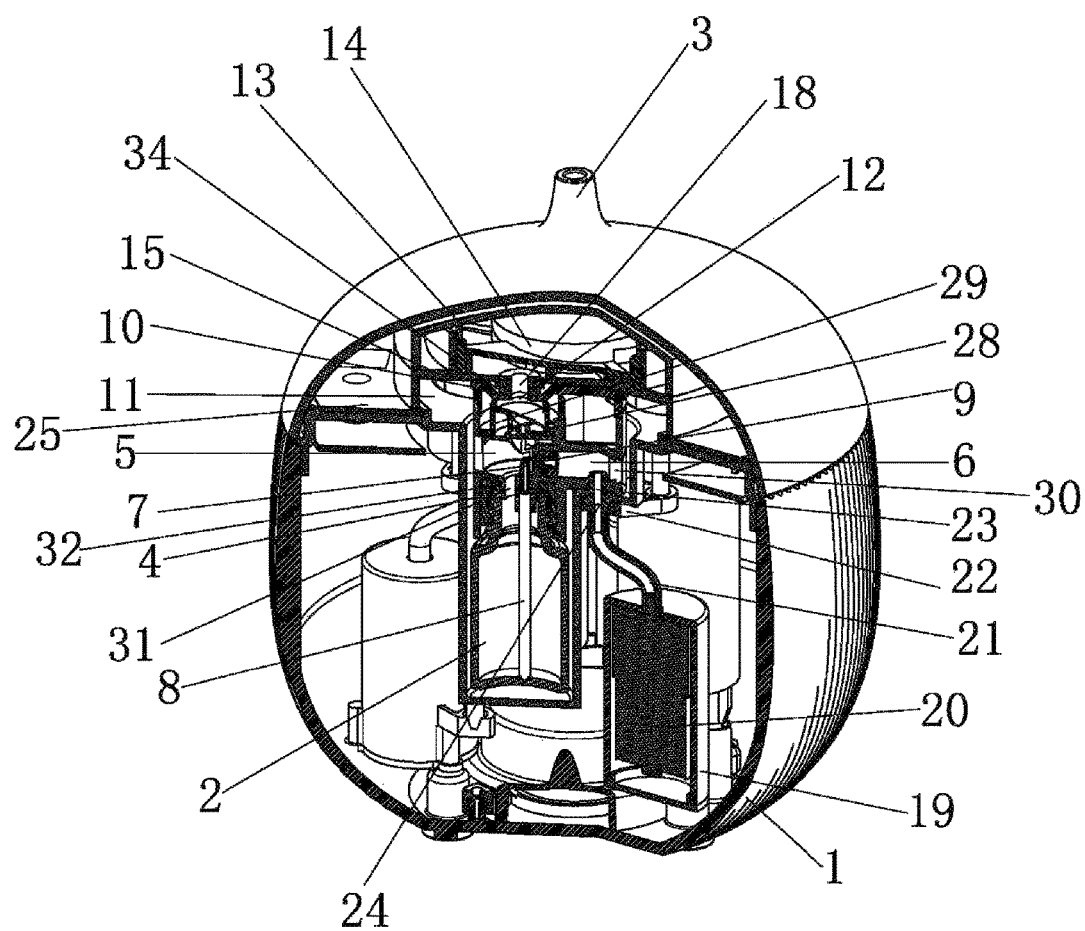
FIG. 1 is a structural schematic of an aroma diffuser with an adjustable essential oil gas proportion provided by the present invention.
Figure 2:
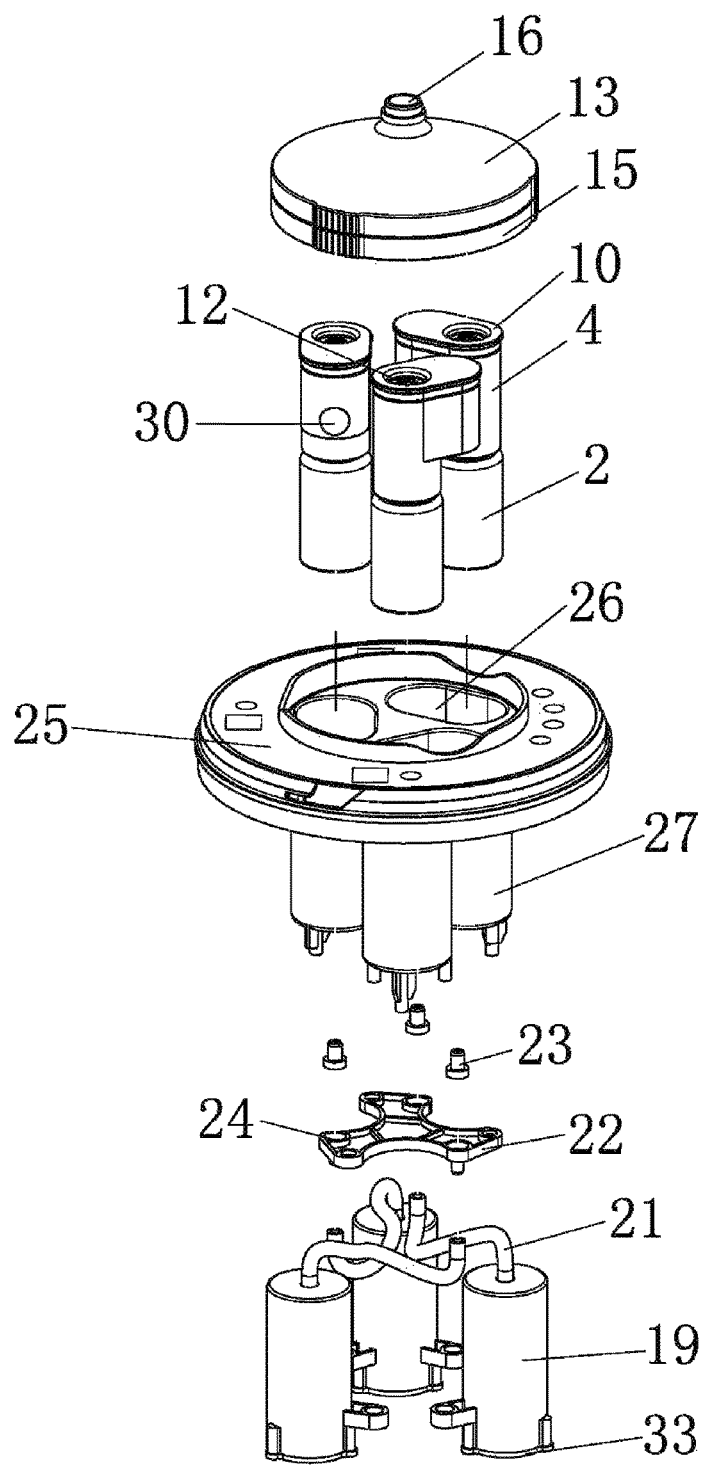
FIG. 2 is a schematic for the internal structure of an aroma diffuser with an adjustable essential oil gas proportion provided by the present invention.

As shown in FIG. 1 and FIG. 2, the present invention discloses an aroma diffuser with an adjustable essential oil gas proportion, comprising a housing 1 and an electric control element disposed on a side face of the housing 1, and inside the housing 1 there are at least two essential oil bottles 2, gasification elements corresponding to the essential oil bottles 2, pump elements corresponding to the gasification elements and a fragrance mixing element. To be specific, the quantity of the gasification elements is same as the quantity of the essential oil bottles 2, and the quantity of the pump elements are same as the quantity of the gasification elements. The lower end of each of the gasification elements is connected to an open end of the corresponding essential oil bottle 2, each of the gasification elements communicates with the open end of the corresponding essential oil bottle 2, and the upper end of each of the gasification elements stretches into the cavity 11 at the lower end of the fragrance mixing element and fits with an end face of the cavity 11. The lower end of the fragrance mixing element communicates with the upper end of each of the gasification elements, and the upper end of the fragrance mixing element communicates with a centralized fragrance diffusion outlet 3 at the upper end of the housing 1. Each of the pump elements is connected to the corresponding gasification element and the electric control element, and each of the pump elements communicates with the corresponding gasification element. In this embodiment, as shown in FIG. 1, the housing 1 is approximately in a round shape, and certainly may be in other shapes, too.

In this embodiment, as shown in FIG. 1 and FIG. 2, inside the housing 1 there is a support plate 25. The support plate 25 comprises first grooves 26 corresponding to all gasification elements. The gasification elements are placed in the first grooves 26. The bottom surfaces of the first grooves 26 comprise second grooves 27. The essential oil bottles 2 connected to the lower ends of the gasification elements are placed inside the second grooves 27, which are for receiving the gasification elements and the essential oil bottles 2. The structure is compact.

Figure 3:
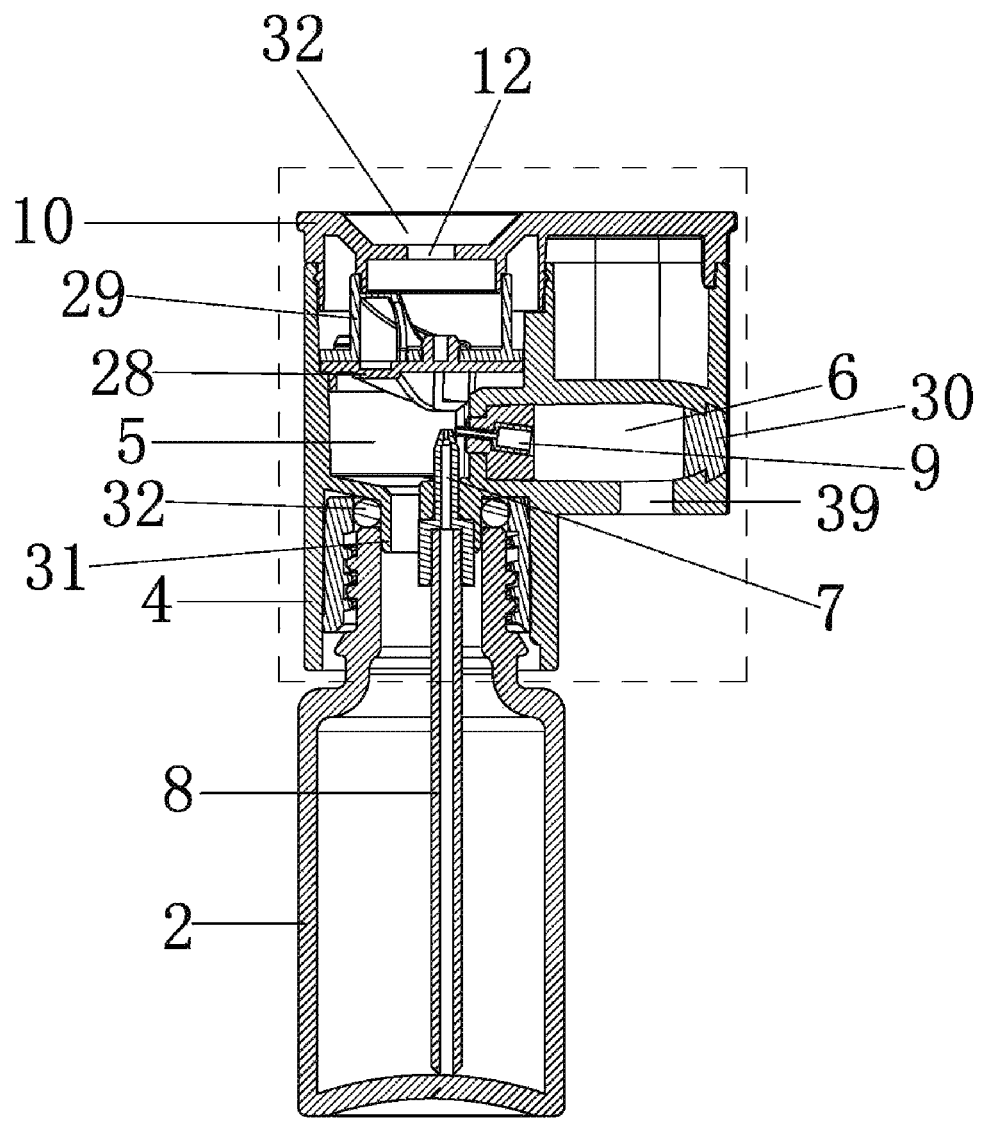
FIG. 3 is a structural schematic for connection between a gasification element and the open end of the corresponding essential oil bottle in the present invention.

As shown in FIG. 3, the gasification element comprises a gasification chamber body 4. The lower end of the gasification chamber body 4 is connected to an open end of the corresponding essential oil bottle 2. The gasification chamber body 4 comprises a gasification chamber 5, an air chamber 6, and an essential oil nozzle 7, an air inlet 39 and an oil conduit 8 disposed at the lower end of the gasification chamber body 4. The gasification chamber 5 and the air chamber 6 are connected through an air nozzle 9. The upper end of the essential oil nozzle 7 stretches into the gasification chamber 5 and is close to the air nozzle 9. The gasification chamber 5 communicates with the essential oil nozzle 7 and an open end of the corresponding essential oil bottle 2 respectively. The air inlet 39 communicates with the air chamber 6. The oil conduit 8 is disposed at the lower end of the essential oil nozzle 7. The oil conduit 8 communicates with the essential oil nozzle 7. The lower end of the oil conduit 8 stretches into the corresponding essential oil bottle 2. The surface of the lower end of the oil conduit 8 is close to the bottom surface of the essential oil bottle 2. It makes for the suction of liquid essential oil. In this case, when airstream passes the air nozzle 9 and is sprayed out at a high speed, negative pressure will be formed above the essential oil nozzle 7. As a result, the oil conduit 8 will suck the liquid essential oil out from the essential oil bottle 2 and spray it to the gasification chamber 5 via the essential oil nozzle 7. Meanwhile, the jet stream sprayed from the air nozzle 9 will gasify the essential oil sprayed from the essential oil nozzle 7 into tiny particles, which will become essential oil gas.

The gasification element further comprises a gasification chamber cover 10. The gasification chamber cover 10 is snapped into the gasification chamber body 4. The upper end of the gasification chamber cover 10 stretches into a cavity 11 at the lower end of the fragrance mixing element and fits with an end face of the cavity 11. The upper end of the gasification chamber cover 10 comprises a fragrance outlet 12. The fragrance outlet 12 communicates with the gasification chamber 5 and the fragrance mixing element respectively.

Figure 4:
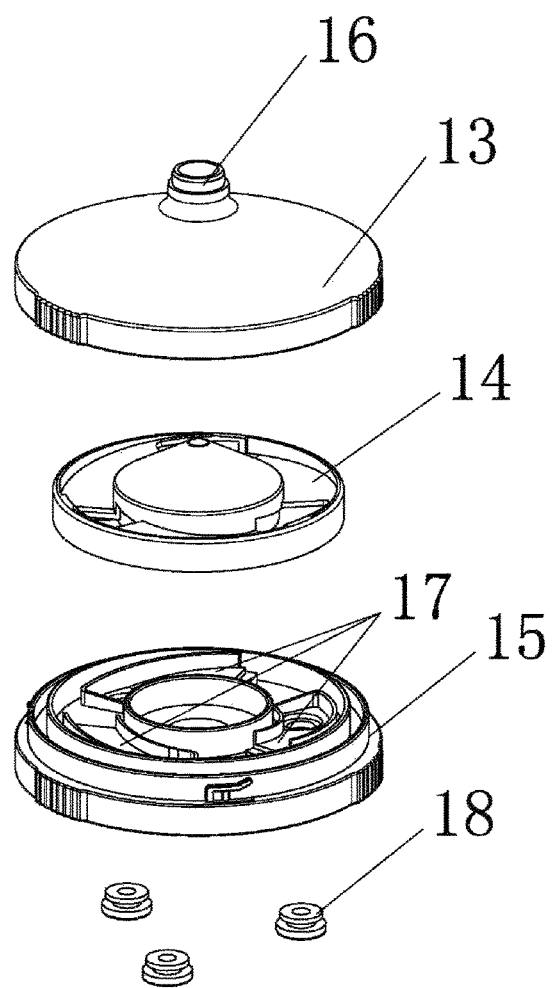
FIG. 4 is an exploded schematic of a fragrance mixing element in the present invention.

As shown in FIG. 4, the fragrance mixing element comprises a mixing chamber cover 13, a mixing blade 14 and a mixing chamber base 15. The mixing chamber cover 13 is snapped into the mixing chamber base 15. The mixing blade 14 is snapped into the mixing chamber base 15 and received in the mixing chamber enclosed by the mixing chamber cover 13 and the mixing chamber base 15. The mixing chamber base 15 is disposed on the support plate 25. The upper end of the mixing chamber cover 13 comprises a fragrance converging port 16 inlaid in the centralized fragrance diffusion outlet 3 at the upper end of the housing 1. The fragrance converging port 16 communicates with the centralized fragrance diffusion outlet 3 and the mixing chamber respectively. The upper end of the mixing chamber base 15 comprises fragrance access passages 17 corresponding to the gasification elements. Specifically, the quantity of the fragrance access passages 17 is equal to the quantity of the gasification elements. The fragrance access passages 17 communicate with the mixing chamber. The lower end of the mixing chamber base 15 comprises a cavity 11, enclosing the first groove 26 to underneath of the cavity. The upper end of the gasification chamber cover 10 stretches into the cavity 11 and fits with an end face of the cavity 11. The end face of the cavity 11 comprises a fragrance inlet 18 communicating with the fragrance outlet 12 and the fragrance access passage 17 respectively. The fragrance inlet 15 corresponds to the fragrance outlet 12 and fragrance access passage 17. The essential oil gas discharged from the fragrance outlet 12 enters the fragrance access passage 17 via the fragrance inlet 18. When the essential oil gas in the fragrance access passage 17 arrives at the inside of the mixing chamber, it rotates and is mixed in the spiral channel of the mixing blade 14. After mixing, it is diffused to the air from the centralized fragrance diffusion outlet 3 via the fragrance converging port 16, thereby achieving the effect of mixed compound essential oil.

Figure 5:
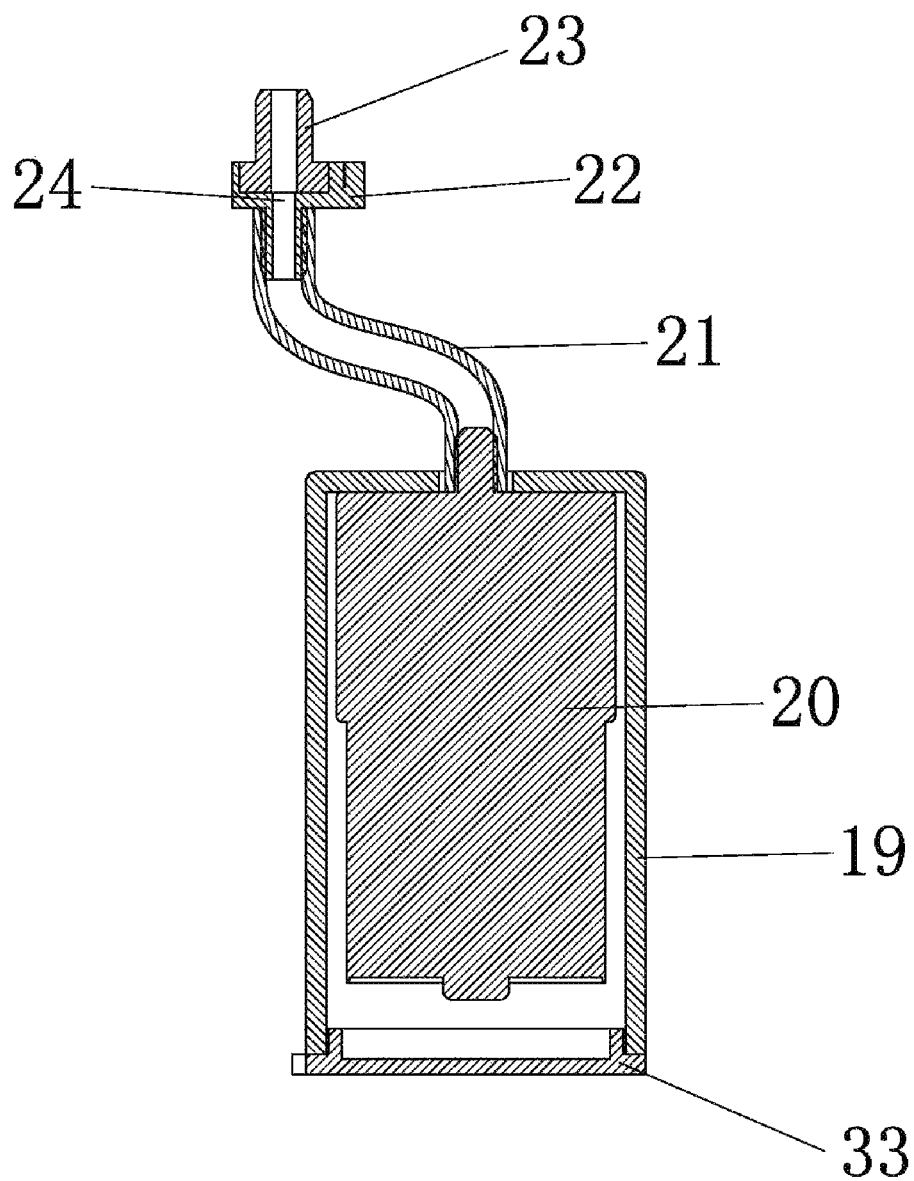
FIG. 5 is a structural schematic of a pump element in the present invention.
Figure 6:
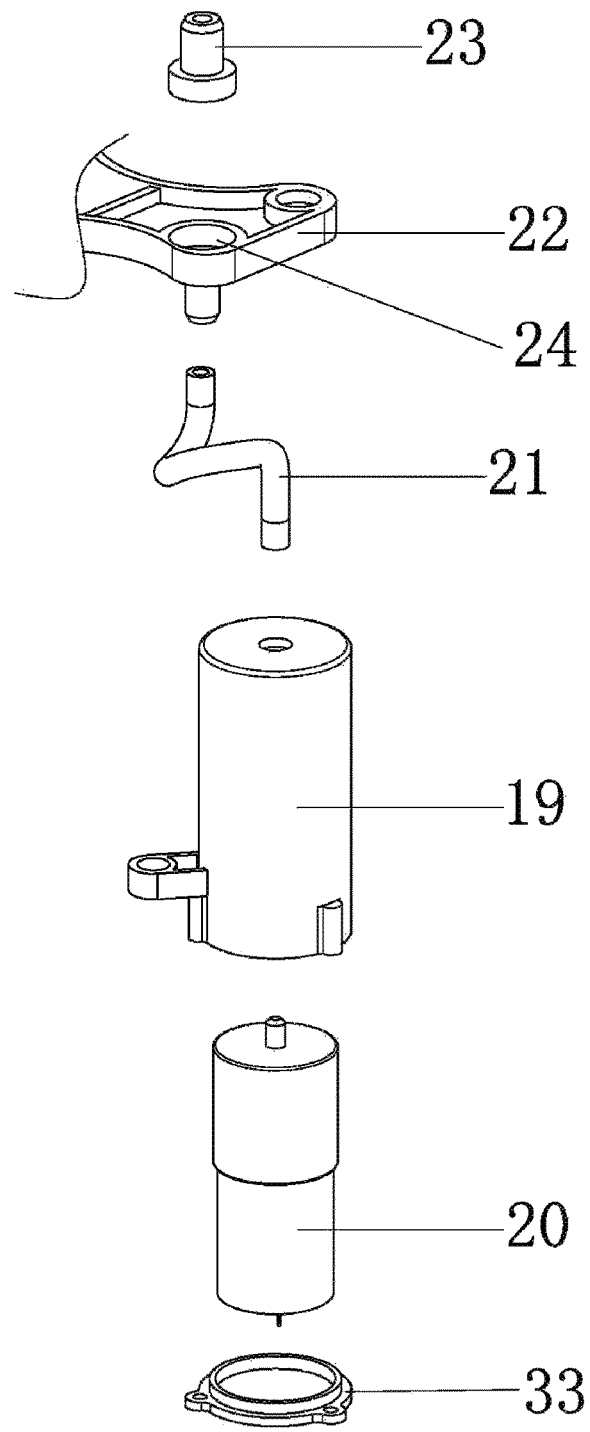
FIG. 6 is an exploded schematic of a pump element in the present invention.

As shown in FIG. 5 and FIG. 6, the pump element comprises a pump mounting rack 19 received in the housing 1, and a pump body 20, an air duct 21, a holder 22 and an air output nozzle 23 received in the pump mounting rack 19. In this embodiment, the pump mounting rack 19 is disposed on the bottom surface of the housing 1. The holder 22 is disposed on the lower end of the first groove 26 of the corresponding gasification element and there is a mounting hole 24 on the holder 22. The structure is stable and well fixed. One end of the air duct 21 is connected to the pump body 20 and another end of the air duct sticks out from an upper end of the pump mounting rack 19 and is fixed onto the mounting hole 24. The air duct 21 communicates with the mounting hole 24. The lower end of the air output nozzle 23 is fixed onto the mounting hole 24. The upper end of the air output nozzle 23 passes through the first groove 26, is inlaid in the air inlet 39 and stretches into the air chamber 6. The air output nozzle 23 communicates with the air chamber 6 and the mounting hole 24 respectively. Through this structure, the airstream output by the pump body 20 enters the air chamber 6 via the air duct 21, the mounting hole 24 and the air output nozzle 23.

In this embodiment, as shown in FIG. 1 and FIG. 3, the gasification chamber body 4 further comprises a lower vortex body 28 and an upper vortex body 29. The lower vortex body 28 and the upper vortex body 29 are disposed inside the gasification chamber 5 from bottom to top in turn. The lower end of the upper vortex body 29 is connected to the lower vortex body 28. The upper end of the upper vortex body 29 is connected to the gasification chamber cover 10. The upper vortex body 29, the lower vortex body 28 and the gasification chamber 5 are mutually communicable. The gasified essential oil gas particles form a vortex airstream under action of the lower vortex body 28 and the upper vortex body 29 to make for discharge from the fragrance outlet 12.

Figure 7:
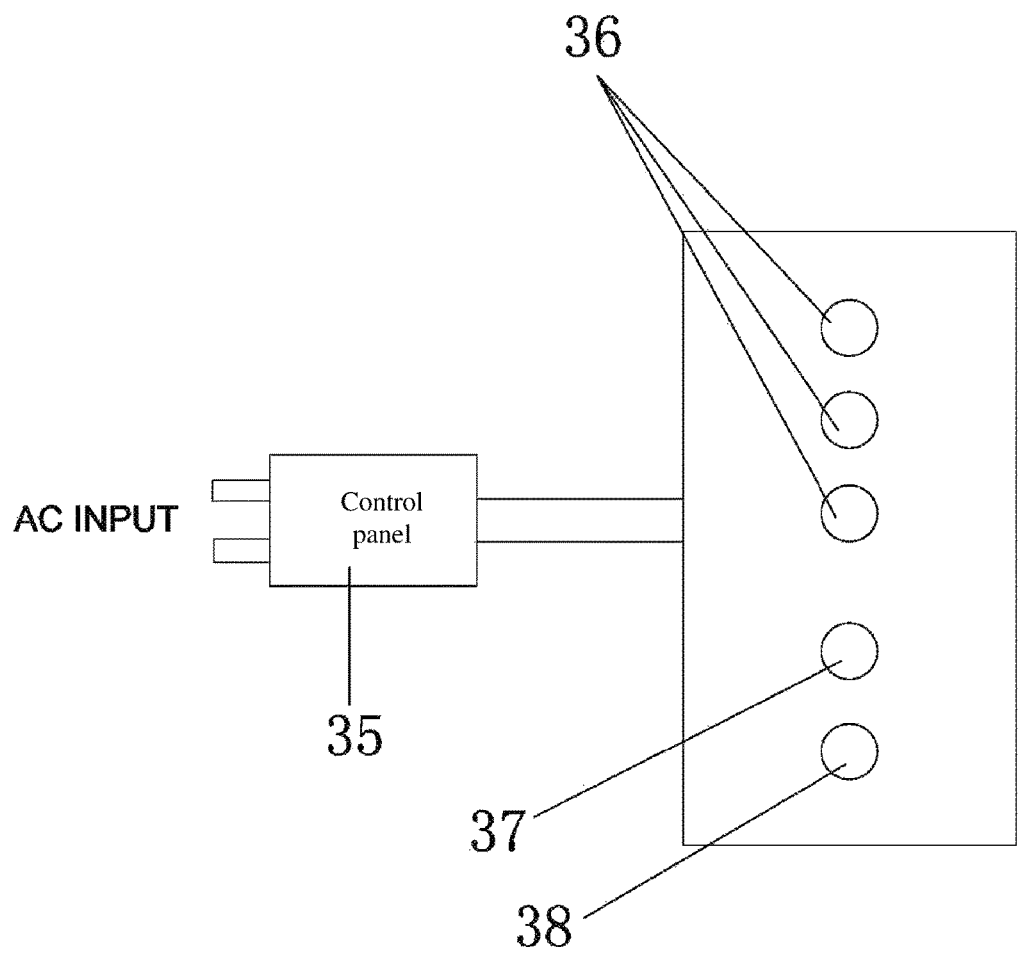
FIG. 7 is a structural schematic of an electric control element in the present invention.

In this embodiment, as shown in FIG. 7, the electric control element comprises a control panel 35, a pump flow regulating button 36 corresponding to each of the pump elements, a time setting button 37 and a power switch 38. The pump flow regulating button 36 is used to regulate the outputted gas flow so as to suck out a corresponding amount of liquid essential oil. The time setting button 37 is used to set working time. The pump flow regulating button 36, the time setting button 37 and the power switch 38 are all connected to the control panel 35. The control panel 35 is connected to all pump elements.

In this embodiment, as shown in FIG. 1 and FIG. 3, the gasification chamber body 4 further comprises a pressure plunger 30. The pressure plunger 30 is disposed on a side face of the gasification chamber body 4 and one end of the pressure plunger 30 is inside the air chamber 6. The center of the pressure plunger 30 and the center of the air nozzle 9 form a straight line. The pressure plunger 30 can help the air in the air chamber 6 spray out from the air nozzle 9 at a high speed.

In this embodiment, as shown in FIG. 1 and FIG. 3, there is an annular flange 31 on bottom surface of the gasification chamber 5. The annular flange 31 is inlaid in the open end of the corresponding essential oil bottle 2 so that the gasification chamber 5 communicates with the open end of the essential oil bottle 2 and the partial essential oil gas becoming liquid essential oil when it collides with the inner wall of the gasification chamber 5 can flow back to the essential oil bottle 2 and is used cyclically without waste.

Further, in order to improve sealing performance, an O ring 32 is disposed between the annular flange 31 and the corresponding essential oil bottle 2.

In this embodiment, as shown in FIG. 1 and FIG. 3, the lower end of the gasification chamber body 4 comprises a first thread, and the open end of the corresponding essential oil bottle 2 comprises a corresponding second thread. Specifically, an internal thread is disposed on a lower end of the gasification chamber body 4, and a corresponding external thread is disposed on an open end of the corresponding essential oil bottle 2, and the first thread is connected to the second thread. The sealing performance is good. It makes for dismounting of the essential oil bottle 2 and charging of liquid essential oil.

In this embodiment, in order to improve sealing performance, a seal ring is disposed between the oil conduit 8 and the essential oil nozzle 7.

In this embodiment, as shown in FIG. 5 and FIG. 6, a pump cover 33 is disposed at the lower end of the pump mounting rack 19. It can guarantee the working performance and sealing performance of the pump body and is not easily damaged.

In this embodiment, as shown in FIG. 1 and FIG. 3, the upper end of the gasification chamber cover 10 comprises a cover groove 34, the bottom surface of the cover groove 34 comprises a fragrance outlet 12, the fragrance outlet 12 fits with the lower end of the fragrance inlet 18, and the fragrance outlet 12 communicates with the gasification chamber 5 and the fragrance inlet 18.

The present invention further discloses an aroma diffusing method, comprising:

Providing an aroma diffuser, comprising: a housing 1, at least two essential oil bottles 2, gasification elements, pump elements, a fragrance mixing element and an electric control element.

Charging different liquid essential oils into different essential oil bottles 2;

Regulating the electric control element according to the actually needed optimum mixing proportion and working time of the essential oil;

Under action of the electric control element, importing ambient air into air chambers 6 of the gasification elements through pump bodies 20 of the pump elements and forming jet stream;

Spraying the jet stream above an essential oil nozzle 7 of each of the gasification elements to form negative pressure so as to suck liquid essential oil out from the respective essential oil bottles 2 and gasify the liquid essential oil into essential oil gas.

Mixing the gasified essential oil gases entering the mixing chamber of the fragrance mixing element, and diffusing the mixed essential oil gas to ambient air through a centralized fragrance diffusion outlet 3 of the housing 1 to complete aroma diffusing process.

To be specific, in this embodiment, different liquid essential oils are charged into different essential oil bottles 2 respectively and every pump flow regulating button 36 and time setting button 37 of the electric control element are regulated according to the actually needed optimum mixing proportion and working time of essential oil; power switch 38 of the electric control element is started, and each of the pump bodies 20 of the pump elements outputs corresponding air flow under action of the control panel 35 of the electric control element. The air flow is output into the air chamber 6 via the air duct 21, the mounting hole 24 and the air output nozzle 23 of the pump element in turn. The airstream in the air chamber 6 is sprayed out from the air nozzle 9 at a high speed and forms negative pressure above the essential oil nozzle 7. At the moment, the oil conduit 8 of the gasification element sucks the liquid essential oil out from the essential oil bottle 2 and sprays it out from the gasification chamber 5 through the essential oil nozzle 7. Meanwhile, the jet stream sprayed out from the air nozzle 9 gasifies the liquid essential oil sprayed out from the essential oil nozzle 7 into tiny particles, which will become essential oil gas. When essential oil gas collides with the inner wall of the gasification chamber 5, part of it will become liquid essential oil and flow back to the essential oil bottle 2, while the remaining essential oil gas will be discharged from the fragrance outlet 12 under action of the lower vortex body 28 and the upper vortex body 29. Different essential oil gases enter different fragrance access passages 17 of the fragrance mixing element via different fragrance inlets 18 of the fragrance mixing element. When the essential oil gases in different fragrance access passages 17 arrive at the mixing chamber, they rotate in the spiral channel set by the mixing blade 14 of the fragrance mixing element and are mixed. After mixing, the gases are diffused to the air from the centralized fragrance diffusion outlet 3 via the fragrance converging port 16 of the fragrance mixing element, thereby completing the process of aroma diffusion.

Also as shown in FIG. 1 and FIG. 2, in this embodiment, this aroma diffuser has three essential oil bottles 2. Accordingly, the numbers of the gasification elements and the first grooves 26, the second grooves 27, the fragrance inlets 18, the fragrance access passages 17 and the pump flow regulating buttons 36 on the pump element support plate 25 are all three. After the three essential oil bottles 2 are connected to the corresponding gasification elements, they are placed in the corresponding first grooves 26 and second grooves 27. The holder 22 of each of the pump elements is disposed on a lower end of the first groove 26 receiving the corresponding gasification element. The holders 22 of the three pump elements are integral. An upper end of the air output nozzle 23 of each pump element passes through the first groove 26, is inlaid in the air inlet 39 and stretches into the air chamber 6. Three different liquid essential oils are put into three essential oil bottles 2. The three pump flow regulating buttons 36 and time setting buttons 37 are regulated and set according to the actually needed optimum mixing proportion and working time of the essential oil. The power switch 38 is on. The three pump bodies 20 output corresponding air flow under action of the control panel 35. The air flow is output into the air chamber 6 via the air duct 21, the mounting hole 24 and the air output nozzle 23 in turn. The airstream in the air chamber 6 is sprayed out from the air nozzle 9 at a high speed and forms negative pressure above the essential oil nozzle 7. At the moment, the oil conduit 8 sucks the liquid essential oil out from the essential oil bottle 2 and sprays it out from the gasification chamber 5 through the essential oil nozzle 7. Meanwhile, the jet stream sprayed out from the air nozzle 9 gasifies the liquid essential oil sprayed out from the essential oil nozzle 7 into tiny particles, which will become essential oil gas. When essential oil gas collides with the inner wall of the gasification chamber 5, part of it will become liquid essential oil and flow back to the essential oil bottle 2, while the remaining essential oil gas will be discharged from the fragrance outlet 12 under action of the lower vortex body 28 and the upper vortex body 29. Three kinds of essential oil gases enter three fragrance access passages 17 via three fragrance inlets 18. When the essential oil gases in the three fragrance access passages 17 arrive at the mixing chamber, they rotate in the spiral channel set by the mixing blade 14 and are mixed. After mixing, the gases are diffused to the air from the centralized fragrance diffusion outlet 3 via the fragrance converging port 16, thereby achieving the needed effect of compound essential oil after mixing.

During use of the aroma diffuser disclosed by the present invention, and implementation of the aroma diffusing method, the following steps may be referred to:

A. Separately charging different liquid essential oils into the essential oil bottles 2;

B. Calculating the optimum mixing proportion and working time of each essential oil according to the actual environmental need and the characteristics of the essential oils (an optional step);

C. Adjusting the pump flow regulating button 36 and the time setting button 37 according to the mixing proportion and working time in step B;

D. Starting the power switch 38 after setting. Under action of the pump elements, the gasification elements and the fragrance mixing element, the effect of a compound essential oil may be achieved by mixing essential oils according to the proportion in the set working time.

Embodiment 1

A method for using the aroma diffuser, comprising:

A. Putting grapefruit, peppermint and cedar liquid essential oils into three essential oil bottles 2 separately;

B. Calculating the optimum mixing proportion of grapefruit, peppermint and cedar essential oils 30%, 40%, 30% and the optimum working time 2 h in a space of 50 square meters according to the characteristics of grapefruit, peppermint and cedar essential oils;

C. Adjusting the pump flow regulating button 36 and the time setting button 37 according to the mixing proportion and working time in step B;

D. Starting power switch 38 after setting. Under action of the pump elements, the gasification elements and the fragrance mixing element, the effect of a compound essential oil may be achieved in 2 h by mixing grapefruit, peppermint and cedar essential oils in a proportion of 3:4:3.

Embodiment 2

A method for using the aroma diffuser, comprising:

A. Putting grapefruit and peppermint liquid essential oils in two essential oil bottles 2 separately;

B. Calculating the optimum mixing proportion of grapefruit and peppermint essential oils 60% and 40% and the optimum working time 2 h in a space of 50 square meters according to the characteristics of grapefruit and peppermint essential oils;

C. Adjusting the pump flow regulating button 36 and the time setting button 37 according to the mixing proportion and working time in step B;

D. Starting power switch 38 after setting. Under action of the pump elements, the gasification elements and the fragrance mixing element, the effect of a compound essential oil may be achieved in 2 h by mixing grapefruit and peppermint essential oils in a proportion of 6:4.

Figure 8:
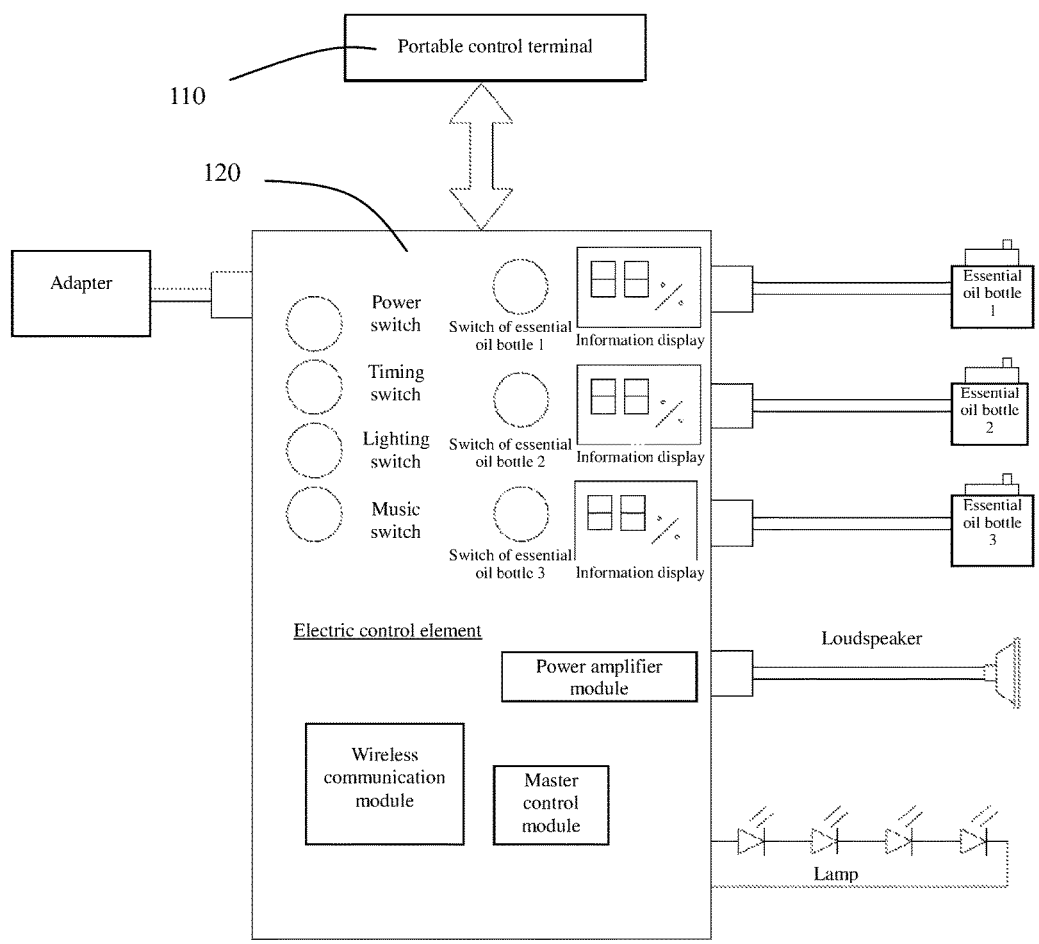
FIG. 8 is a schematic of an aroma diffusing system provided by another embodiment of the present invention.

Still further, as shown in FIG. 8, another embodiment of the present invention provides an aroma diffusing system. This system comprises a portable control terminal 110 and an aroma diffuser 120. The portable control terminal 110 is a mobile terminal in fact, for example: a smart phone installed with corresponding APP.

The aroma diffuser 120 is a stand-alone aroma diffuser and also comprises a wireless communication module so that it can realize wireless interaction with a mobile terminal. The functional components of the aroma diffuser 120 are similar to the aroma diffuser provided by the foregoing embodiment. For example, they both comprise essential oil bottles for accommodating essential oil, gasification elements for extracting essential oil from the essential oil bottles and gasifying the extracted essential oil and an electric control element for controlling the gasification elements. Main difference: The electric control element comprises a wireless communication module, used to receive orders sent in a wireless mode and executed by the electric control element. This wireless communication module may be a WiFi module and/or a Bluetooth module.

Figure 9:
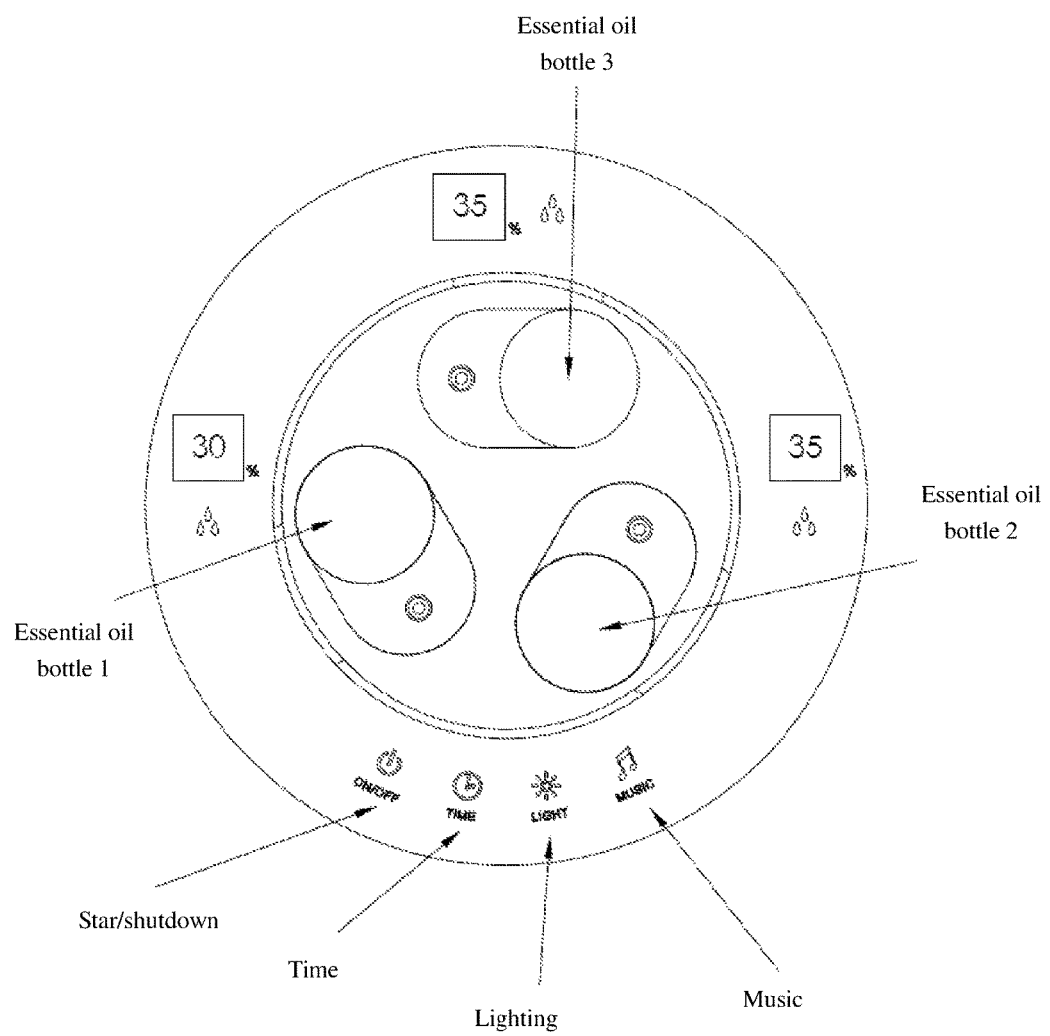
FIG. 9 is an interface of a portable control terminal used by the aroma diffusing system shown in FIG. 8.

Therefore, the aroma diffuser 120 may undertake wireless interaction with the portable control terminal 110. This portable control terminal 110 may be a mobile terminal installed with corresponding APP, such as: smart phone or tablet computer. FIG. 9 is a concept diagram of an interface of the corresponding APP. This mobile terminal is used to send orders to the aroma diffuser 120 in a wireless mode, for execution of the electric control element.

In this embodiment, there are at three essential oil bottles and they are used to accommodate different essential oils; the quantity of the gasification elements is same as the quantity of the essential oil bottles and each of the gasification elements corresponds to an essential oil bottle; the electric control element may independently control the start, shutdown and gasification speed of each of the gasification elements.

The electric control element comprises: a power switch that may electrically connect or disconnect the gasification elements according to the order the wireless communication module receives; a timing switch that may control the gasification elements according to the order the wireless communication module receives; a lighting switch that may control the lighting of the aroma diffuser at a fixed time according to the order the wireless communication module receives; a music switch that may control the loudspeaker of the aroma diffuser at a fixed time according to the order the wireless communication module receives. It can be understood that in other embodiments, one or a plurality of switches may be selected according to need.

The aroma diffusing method of the aroma diffusing system shown in FIG. 8 comprises the following steps:

Establishing wireless communication connection between a mobile terminal (i.e.: portable control terminal 110) and an aroma diffuser 120;

Receiving user input and generating a corresponding order through the mobile terminal 110 and sending the order in a wireless mode;

Receiving the order through the wireless communication module of the aroma diffuser and executing the order through the electric control element of the aroma diffuser;

Further, feeding back order execution result to the mobile terminal through the wireless communication module of the aroma diffuser; receiving the order execution result through the mobile terminal and giving a corresponding prompt in the mobile terminal;

As different essential oil bottles accommodate different essential oils, different aroma diffusing modes may be realized through controlling the gasification elements. For example, the orders sent by the mobile terminal include the orders for controlling gasification efficiency of corresponding gasification elements.

It is understood that the orders sent by a mobile terminal may include any of the following orders or combinations of two or more orders: order for shutting down or starting part or all of the gasification elements; order for controlling the time of continuous operation of part or all of the gasification elements; order for controlling cyclic operation of part or all of the gasification elements; order for controlling lighting color of the aroma diffuser; order for starting or shutting down part or all of the gasification elements at a fixed time.

The user may directly input color information in a mobile terminal, for example: information name or color code value. Alternately, the mobile terminal may identify the desired colors. For example, the user may open a picture or photo through APP, thereby APP can identify the color of the picture and generate a corresponding lighting color order according to this color.

In another operation scenario, a corresponding lighting color order may be generated according to video picture. For example, the user may play a video file through APP and generate a corresponding lighting color order according to the content of the video picture.

Further, the user may also read an audio file in a mobile terminal through APP and send out an audio signal in a wireless mode; the wireless communication module of the aroma diffuser receives this audio file and may play audio signals through the loudspeaker of the aroma diffuser.

To summarize, a user may start and shut down the aroma diffuser through APP, may set the working time and stop time of aroma diffusion, and even may set the time of cyclic operation, for example, stop for 5 min whenever after working for 2 h, and repeat this process continuously.

Through mobile phone APP, the color of lighting of the aroma diffuser may be set. There is a color disc in the APP. When a color in the color disc is clicked, the lighting will be changed into the designated color. Through mobile phone APP, the brightness and color saturation of lighting may be adjusted. Further, the color of a picture may be acquired from camera lens and product lighting may be converted into a color acquired by the camera. Preferably, evening glow, early morning, sea waves and other lighting modes are built in. When the mode of evening glow is selected, product lighting is switched to the lighting in the evening glow mode. When forest mode is selected, product lighting is switched to the lighting in a forest mode. More preferably, video clips are built in and lighting will be interactive along with the play of video. During interaction between lighting and video, the colors of lighting will vary accordingly with the pictures of the video. The lighting is not in a single color. Instead, its color effect is same as that of video pictures and the lighting effect changes dynamically with the changes of video.

During implementation of the present invention, APP is adopted to control fragrance mixing proportion. The diffusion proportion of oil in a single bottle may be regulated separately, or alternately the diffusion proportion of oil in a plurality of bottles may be regulated. The diffusion concentration is regulated in the range of 1%-99%.

Preferably, the APP of the mobile terminal has one-key fragrance mixing modes. To be specific, the APP has a plurality of built-in fragrance mixing modes, such as: romantics, early morning, refreshing, elation, sleep and mediation. When a fragrance mixing mode is selected, the program will automatically invoke information and complete setting of fragrance mixing proportion to make you smell the odor you like in a second. Further, one-key treatment mode may be provided, too. To be specific, a number of treatment formulae are saved in APP, such as: dispelling flu, killing bacteria, cleaning, easing anxiety and alleviating respiratory infection. When a symptom is selected, the program will automatically set and complete a complex blending process.

Further, through the fragrance mixing modes preset by APP for different types of people, such as: old people, children, women and men, the aroma diffuser automatically sets different fragrance mixing proportions in a same mode based on the psychological features of the people and releases different fragrance concentrations.

To sum up, the aroma diffuser provided by the present invention opens a brand new intelligent function mode. By selecting a fixed efficacy button in product APP, a corresponding efficacy order may be quickly transferred to the product, and the diffusion function meeting the functional requirements of the order, the music effect corresponding to the order function and the lighting effect corresponding to the order function may be started in the product to jointly achieve an efficacy conforming to the order mode.

Taking "soothing and calming" for example, when "soothing and calming" efficacy is selected in product APP, the efficacy order of "soothing and calming" will be transferred to the electric control element of the aroma diffuser through a Bluetooth or Wi-Fi signal. After receiving the signal, the electric control element starts the pumps of gasification elements through a master control module. The order sent by APP contains an essential oil formula for soothing and calming. This formula corresponds to a relation of blending of two or more than two essential oils at different proportions. Taking "soothing and calming" for example, the relation of this formula is: cedar 30%, marjoram 35% and finger citron 35%. APP will remind the user of putting cedar essential oil in essential oil bottle 1 (Aroma 1), marjoram in essential oil bottle 2 (Aroma 2) and finger citron in essential oil bottle 3 (Aroma 3). After essential oils are placed, the electric control element controls the rotational speed of pump motors through PWM (pulse-width modulation). The rotational speed of pump motors corresponds to oil injection quantity. Oil injection quantity is set pro rata according to the formula, as cedar essential oil 30% in essential oil bottle 1 (Aroma 1), marjoram 35% in essential oil bottle 2 (Aroma 2) and finger citron 35% in essential oil bottle 3 (Aroma 3). After mixed in the mixing chamber in proportion, the essential oils may provide a gas with "soothing and calming" efficacy. Meanwhile, APP invokes music with "soothing and calming" efficacy from the database. The music signal will be transferred to the electric control element through a Bluetooth or Wi-Fi signal. The electric control element starts the power amplifier module through the master control module to drive the loudspeaker and plays soothing and calming music. Meanwhile, APP obtains a soothing and calming lighting color signal from the database and transfers the signal to the electric control element through a Bluetooth or Wi-Fi signal. The electric control element starts LED lighting through the master control module and realizes a lighting mode suitable for a soothing and calming effect. Through one-key control of APP, the product may obtain a fragrant odor blended according to the soothing and calming formula. The odor, the music corresponding to soothing and calming and the lighting color corresponding to soothing and calming jointly achieve an optimum soothing and calming efficacy through the action in three aspects: odor, music and lighting.

Taking "power" for example: When "power" efficacy is selected in product APP, the efficacy order of "power" will be transferred to the electric control element through a Bluetooth or Wi-Fi signal. After receiving the signal, the electric control element starts the pumps of gasification elements through a master control module. The order sent by APP contains an essential oil formula for power. This formula corresponds to a relation of blending of two or more than two essential oils in different proportions. Taking "power" for example, the relation of this formula is: vanilla root 30%, cedar 30% and pine 40%. APP will remind the user of putting vanilla root essential oil in essential oil bottle 1 (Aroma 1), cedar essential oil in essential oil bottle 2 (Aroma 2) and pine essential oil in essential oil bottle 3 (Aroma 3). After essential oils are placed, the electric control element controls the rotational speed of pump motors through PWM (pulse-width modulation). The rotational speed of pump motors corresponds to oil injection quantity. Oil injection quantity is set pro rata according to the formula, as vanilla root essential oil 30% in essential oil bottle 1 (Aroma 1), cedar essential oil 30% in essential oil bottle 2 (Aroma 2) and pine essential oil 40% in essential oil bottle 3 (Aroma 3). After mixed in the mixing chamber in proportion, the essential oils may provide a gas with "power" efficacy. Meanwhile, APP invokes music with "power" efficacy from the database. The music signal will be transferred to the electric control element through a Bluetooth or Wi-Fi signal. The electric control element starts the power amplifier IC through control IC to drive the loudspeaker and plays power music. Meanwhile, APP obtains a power lighting color signal from the database and transfers the signal to the electric control element through a Bluetooth or Wi-Fi signal. The electric control element starts LED lighting through control IC and realizes a lighting mode suitable for a power effect. Through one-key control of APP, the product may obtain a fragrant odor blended according to the power formula. The odor, the music corresponding to power and the lighting color corresponding to power jointly achieve an optimum power efficacy through the action in three aspects: odor, music and lighting.

The foregoing embodiments only represent the preferred embodiments of the present invention. Their descriptions are concrete and detailed, but they shall not be therefore understood as limitations to the scope of the present invention patent. It shall be noted that for those skilled in the art, various changes and modifications may be made to the embodiments without departing from the spirit of the present invention, such as: combinations of different features of the embodiments. All these shall be in the protective scope of the present invention.

What is claimed is:
1. An aroma diffusing method, comprising:
 establishing wireless communication connection between a mobile terminal and an aroma diffuser;
 receiving user input and generating a corresponding order through the mobile terminal and sending the order in a wireless mode;

receiving the order through a wireless communication module of the aroma diffuser and executing the order through an electric control element of the aroma diffuser;

feeding back order execution result to the mobile terminal through the wireless communication module of the aroma diffuser;

receiving the order execution result through the mobile terminal and giving a corresponding prompt in the mobile terminal.

2. The aroma diffusing method according to claim 1, wherein:

the aroma diffuser comprises at least two essential oil bottles for accommodating essential oil;

the aroma diffuser further comprising gasification elements corresponding to the essential oil bottles and each of the gasification elements being used to extract essential oil from a corresponding essential oil bottle and gasify it;

the orders including orders for controlling gasification efficiency of corresponding gasification elements.

3. The aroma diffusing method according to claim 2, wherein the orders include any of the following orders or combinations of two or more orders:

order for shutting down or starting part or all of the gasification elements;

order for controlling the time of continuous operation of part or all of the gasification elements;

order for controlling cyclic operation of part or all of the gasification elements;

order for controlling lighting color of the aroma diffuser;

order for starting or shutting down part or all of the gasification elements at a fixed time.

4. The aroma diffusing method according to claim 1 further comprising:

identifying picture color in the mobile terminal;

the step of generating a corresponding order including generating a corresponding lighting color order according to the color;

the step of executing the order through an electric control element of the aroma diffuser including regulating lighting of the aroma diffuser according to the lighting color order.

5. The aroma diffusing method according to claim 1 further comprising:

playing video in the mobile terminal;

the step of generating a corresponding order including generating a corresponding lighting color order according to the video picture;

the step of executing the order through an electric control element of the aroma diffuser including regulating lighting of the aroma diffuser according to the lighting color order.

6. The aroma diffusing method according to claim 1 further comprising:

reading an audio file in the mobile terminal and sending out an audio signal in a wireless mode;

receiving the audio signal through a wireless communication module of the aroma diffuser and playing the audio signal through a loudspeaker of the aroma diffuser.

7. An aroma diffusing system, comprising an aroma diffuser; the aroma diffuser comprising essential oil bottles for accommodating essential oil, gasification elements for extracting essential oil from the essential oil bottles and gasifying the extracted essential oil, and an electric control element for controlling the gasification elements; wherein the electric control element comprises a wireless communication module used to receive orders sent in a wireless mode and executed by the electric control element; the aroma diffusing system further comprising a mobile terminal for wireless communication with the aroma diffuser, the mobile terminal being used to send orders for execution of the electric control element to the aroma diffuser in a wireless mode.

8. The aroma diffusing system according to claim 7, wherein there are at least two essential oil bottles for accommodating different essential oils; the quantity of the gasification elements being same as the quantity of the essential oil bottles and each of the gasification elements corresponding to an essential oil bottle; the electric control element independently controlling start, shutdown and gasification speed of each of the gasification elements.

9. The aroma diffusing system according to claim 7, wherein the electric control element at least comprises one of the following:

a power switch used to connect or disconnect the gasification elements according to the order received by the wireless communication module;

a timing switch used to control the gasification elements according to the order received by the wireless communication module;

a lighting switch used to control lighting of the aroma diffuser at a fixed time according to the order received by the wireless communication module;

a music switch used to control a loudspeaker of the aroma diffuser at a fixed time according to the order received by the wireless communication module.

* * * * *